United States Patent [19]

Meier

[11] Patent Number: 5,859,299

[45] Date of Patent: Jan. 12, 1999

[54] PROCESS FOR MAKING NITRO AND AMINO SUBSTITUTED BENZAMIDES

[75] Inventor: Dieter Meier, Eimeldingen, Germany

[73] Assignee: Ciba Specialty Chemicals Corporation, Tarrytown, N.Y.

[21] Appl. No.: 911,887

[22] Filed: Aug. 15, 1997

[30] Foreign Application Priority Data

Aug. 17, 1996 [GB] United Kingdom .................... 9617324
Nov. 29, 1996 [GB] United Kingdom .................... 9624885

[51] Int. Cl.$^6$ .................................................. C07C 231/02
[52] U.S. Cl. ........................ 564/142; 564/143; 564/163; 564/166; 564/415; 564/416
[58] Field of Search .................... 564/143, 415, 564/416, 166, 163, 142

[56] References Cited

U.S. PATENT DOCUMENTS 4,278,683  7/1981  Stoltefuss et al. .................... 424/267
5,472,983  12/1995  Flitter et al. ........................ 514/599

FOREIGN PATENT DOCUMENTS 0117462  9/1984  European Pat. Off. .
0158526  10/1985  European Pat. Off. .
0569792  11/1993  European Pat. Off. ............... 564/142
1265749  4/1968  Germany .

OTHER PUBLICATIONS

J. Am. Chem. Soc., 60, 1938, p. 1081.
Derwent Abst. 123:228829, 1994.
Coll. Czech. Chem. Communs., 1960, vol. 25, pp. 1281–1286.
Chem. Abst. 83:43077m, 1982.
Derwent Abst. 69:26806, 1968.

*Primary Examiner*—Shailendra Kumar
*Attorney, Agent, or Firm*—Kevin T. Mansfield

[57] ABSTRACT

A process is provided for the production of nitrobenzamides or aminobenzamides having the formula:

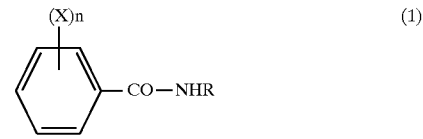

(1)

in which n is 1 or 2, preferably 1, X is an amino or nitro group and R is hydrogen, unsubstituted alkyl or alkyl substituted by halogen, $C_1$–$C_4$-alkoxy, phenyl, carboxyl, $C_1$–$C_4$-alkoxycarbonyl, a mono- or di-$C_1$–$C_4$alkylated amino group or by —$SO_3M$ in which M is hydrogen, an alkali metal atom, ammonium or a cation formed from an amine, which process comprises reacting a nitrobenzoyl chloride having the formula:

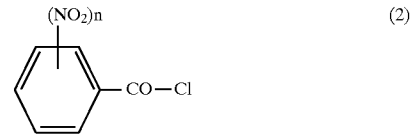

(2)

in which n has its previous significance, with an aqueous solution of an amine having the formula $NH_2$—R in which R has its previous significance, in the presence of an inert organic solvent, to produce a compound having the formula:

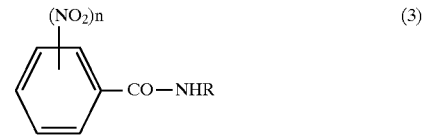

(3)

in which n and R have their previous significance; and finally optionally reducing the nitro group(s) to amino group(s).

11 Claims, No Drawings

PROCESS FOR MAKING NITRO AND AMINO SUBSTITUTED BENZAMIDES

The present invention relates to a new process for the production of nitrobenzamides or aminobenzamides, in particular to a new process for the production of 4-nitro- or 4-amino-N-alkylbenzamides.

Various methods are already known for the production of N-alkylamides of nitrobenzoic acid or of aminobenzoic acid.

For example, in J.A.C.S., 60, 1938, page 1081, there is described a process for the production of N-alkylamides of p-aminobenzoic acid by the reaction of p-nitrobenzoyl chloride with various amines, followed by the reduction of the N-alkylamides of p-nitrobenzoic acid so obtained to give the desired N-alkylamides of p-aminobenzoic acid. The reaction of p-nitrobenzoyl chloride with the amines is conducted in an aqueous medium in the presence of sodium carbonate. The yields of the the N-alkylamides of p-nitrobenzoic acid so obtained are low, probably due to hydrolysis of the p-nitrobenzoyl chloride reactant to p-nitrobenzoic acid.

Moreover, it is also known to produce N-alkylamides of p-nitrobenzoic acid by reacting p-nitrobenzoyl chloride with various amines in a completely organic reaction medium. Again, however, the yields of the the N-alkylamides of p-nitrobenzoic acid so obtained are low. In addition, the use of organic solvent in these known processes is disadvantageous in terms of safety, toxicological and ecological considerations.

Surprisingly, it has now been found that, by the reaction of nitrobenzoyl chlorides with an aqueous solution of an amine, in a reaction medium which contains a specific organic solvent, very high yields of the desired N-alkylamides of p-nitrobenzoic acid are obtained without the safety, toxicological and ecological disadvantages associated with known processes. The addition of a nitrobenzoyl chloride to an aqueous solution of an amine has been found to produce only insignificant amounts of nitrobenzoic acids.

According to the present invention, there is provided a process for the production of nitrobenzamides or aminobenzamides having the formula:

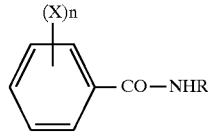

in which n is 1 or 2, preferably 1, X is an amino or nitro group and R is hydrogen, unsubstituted alkyl or alkyl substituted by halogen, $C_1$–$C_4$-alkoxy, phenyl, carboxyl, $C_1$–$C_4$-alkoxycarbonyl, a mono- or di-$C_1$–$C_4$alkylated amino group or by 13 $SO_3M$ in which M is hydrogen, an alkali metal atom, ammonium or a cation formed from an amine, which process comprises reacting a nitrobenzoyl chloride having the formula:

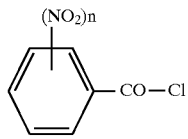

in which n has its previous significance, with an aqueous solution of an amine having the formula $NH_2$—R in which R has its previous significance, in the presence of an inert organic solvent, to produce a compound having the formula:

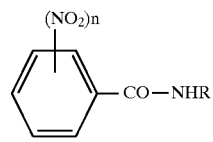

in which n and R have their previous significance; and finally optionally reducing the nitro group(s) to amino group(s).

Preferably M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium or ammonium that is di- or tri-substituted with a mixture of $C_1$–$C_4$alkyl and $C_1$–$C_4$hydroxyalkyl groups.

Preferred unsubstituted alkyl groups R are $C_1$–$C_{12}$-, especially $C_1$–$C_4$-alkyl groups. The alkyl groups may be branched or unbranched. Substituted alkyl groups R may be substituted by halogen such as fluorine, chlorine or bromine, by $C_1$–$C_4$-alkoxy such as methoxy or ethoxy, by phenyl or carboxyl, by $C_1$–$C_4$-alkoxycarbonyl such as acetyl, by a mono- or di-$C_1C_4$alkylated amino group or by —$SO_3M$ in which M has its previous significance. Preferably R is a $C_1$–$C_4$-alkyl group, especially methyl.

Preferably, the reactant of formula (2) is 4-nitrobenzoyl chloride and the amine reactant of formula $NH_2$—R is methylamine.

The organic solvent used in the process according to the present invention may be any organic solvent which is inert to the nitrobenzoyl chloride and amine reactants and which does not give rise to any problems associated with safety, toxicological and ecological factors. Preferred solvents are $C_1$–$C_4$ aliphatic ketones such as acetone, methylethyl ketone, diethyl ketone, dipropyl ketone and dibutyl ketone, since these are inert, toxicologically acceptable and can be safely and readily recovered, for example by distillation techniques, and recycled.

The reaction of a nitrobenzoyl chloride of formula (2) with an aqueous solution of an amine $NH_2$—R according to the present invention is preferably conducted by firstly dissolving the nitrobenzoyl chloride in the organic solvent, preferably anhydrous methylethylketone, at a temperature in the range of from 0 to 60, especially from 30° to 50° C. The concentration of the nitrobenzoyl chloride in the solution so obtained is conveniently within the range of from 40 to 60% by weight, based on the total solution. The solution so obtained is then preferably added, over a period greater than 5 minutes, more preferably over a period ranging from 30 to 60 minutes, to an aqueous solution of the amine $NH_2$—R and an acid acceptor, preferably aqueous sodium hydroxide. During this addition, the reaction temperature is preferably maintained in the range of from 10 to 60, especially from 20° to 40° C. Alternatively, the temperature may be allowed to rise adiabatically, starting from a temperature in the range of from 10° to 40° C. and finishing at a temperature in the range of from 36° to 66° C.

After the addition is complete, the reaction mixture is preferably diluted with water and the organic solvent is removed, for instance by distilling it out from the reaction mixture.

The reduction of the nitro compound of formula (3) to the corresponding amino compound of formula (1) may be effected by any standard technique, for example by hydrogenation or by reaction with stannous chloride and hydrochloric acid, as described in J.A.C.S., 60, 1938, page 1081.

Preferably, however, the nitro compound of formula (3) is reduced, without prior isolation, using iron and acetic acid according to the Bechamps reduction technique.

The compounds of formula (1) obtained by the process of the present invention are useful as intermediates for the production of a wide range of valuable end products. Merely by way of example, the amino compounds of formula (1) may be reacted with 4,4'-chlorotriazinylamino-2,2'-disulfostilbene compounds to produce valuable ultraviolet absorbers or fluorescent whitening agents.

The following Example further illustrates the present invention. Parts and percentages shown therein are by weight unless otherwise stated.

EXAMPLE 93 g of 4-nitrobenzoyl chloride are dissolved in 120 mls of anhydrous methylethylketone at 40° C. This solution is then added, over a period of from 30 to 60 minutes, to an aqueous solution containing 16.8 g of methylamine and 22 g of sodium hydroxide in 500 mls of water. During the addition, the temperature of the reaction mixture is held in the range of from 20° to 40° C. After the completion of the addition, the reaction is diluted with 350 mls of water and the methylethylketone solvent is distilled out from the reaction mixture until the internal temperature of the reaction mixture reaches 100° C. The pH of the reaction mixture is adjusted to 4.0 to 5.0 using acetic acid and the total reaction mixture is then fed into a Bechamps reduction system containing 80 g of iron and 5 g of acetic acid. The Bechamps reduction is conducted electrochemically, progressively in step with the applied voltage, using a grid potential of 100 mV (thalium chloride reference probe), at a temperature of 98° to 100°0 C., the addition time being 1 hour. Finally, the reaction mixture is rendered alkaline (to phenolphthalein) by the addition of aqueous sodium hydroxide and the iron sludge which forms is separated off by filtration at 90° to 95° C. The separated iron sludge is washed with water at at 90° to 95° C. and the respective wash water and the filtrate are combined and salted-out with 15% sodium chloride.

The product, 4-amino-N-methylbenzamide, is isolated by cooling the salted-out reaction mixture to 10° C. and then filtering off the solid material, using a belt filter.

In this way, there are obtained 70 g of 4-amino-N-methylbenzamide having m.p. 179° C. (99.9% purity according to liquid chromatographic analysis). Liquid chromatographic analysis of the product also showed the presence of 4-nitro-N-methylbenzamide, 4-nitrobenzoic acid and 4-aminobenzoic acid, each in an amount of less than 0.02% by weight.

I claim:

1. A process for the production of nitrobenzamides or aminobenzamides having the formula:

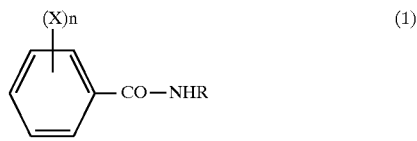 (1)

in which n is 1 or 2, X is an amino or nitro group and R is hydrogen, unsubstituted alkyl or alkyl substituted by halogen, $C_1$–$C_4$-alkoxy, phenyl, carboxyl, $C_1$–$C_4$-alkoxycarbonyl, a mono- or di-$C_1$–$C_4$-alkylated amino group or by —$SO_3M$ in which M is hydrogen, an alkali metal atom, ammonium or a cation formed from an amine, which process comprises reacting a nitrobenzoyl chloride having the formula:

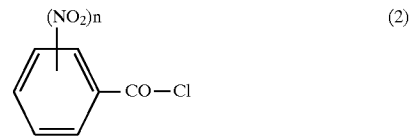 (2)

in which n has its previous significance, with an aqueous solution of an amine having the formula $NH_2$—R in which R has its previous significance, in the presence of an inert organic solvent selected from the group consisting of acetone, methyl ethyl ketone, diethyl ketone, dipropyl ketone or dibutyl ketone, and in the presence of aqueous sodium hydroxide as acid acceptor, to produce a compound having the formula:

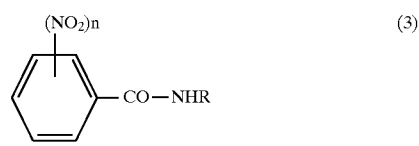 (3)

in which n and R have their previous significance; and finally optionally reducing the nitro group(s) to amino group(s).

2. A process according to claim 1 in which n is 1.

3. A process according to claim 1 in which R is a $C_1$–$C_4$-alkyl group.

4. A process according to claim 3 in which R is methyl.

5. A process according to claim 4 in which the reactant of formula (2) is 4-nitrobenzoyl chloride and the amine reactant of formula $NH_2$—R is methylamine.

6. A process according to claim 1 in which a solution of the nitrobenzoyl chloride having the formula (2) in the inert organic solvent is added, over a period greater than 5 minutes, to an aqueous solution of the amine $NH_2$—R in which R is as defined in claim 1 and sodium hydroxide as acid acceptor.

7. A process according to claim 6 in which the reaction temperature is maintained in the range of from 10 to 60; or the temperature is allowed to rise adiabatically, starting from a temperature in the range of from 10° to 40° C. and finishing at a temperature in the range of from 36° to 66° C.

8. A process according to claim 7 in which the reaction temperature is maintained in the range of from 20° to 40° C.

9. A process according to claim 6 in which, after the addition is complete, the reaction mixture is diluted with water and the organic solvent is removed.

10. A process according to claim 1 in which the nitro compound of formula (3) is reduced, without prior isolation, using iron and acetic acid according to the Bechamps reduction technique.

11. A process according to claim 6, in which the concentration of the nitrobenzoyl chloride of the formula (2) in the inert organic solvent is within the range of from 40 to 60% by weight, based on the total solution.

* * * * *